(12) United States Patent
Linhardt et al.

(10) Patent No.: US 7,919,136 B2
(45) Date of Patent: Apr. 5, 2011

(54) SURFACE TREATMENT OF BIOMEDICAL DEVICES

(75) Inventors: Jeffrey G. Linhardt, Fairport, NY (US); Jay F. Künzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 557 days.

(21) Appl. No.: 11/874,427

(22) Filed: Nov. 20, 2007

(65) Prior Publication Data

US 2008/0143957 A1   Jun. 19, 2008

Related U.S. Application Data

(60) Provisional application No. 60/870,172, filed on Dec. 15, 2006.

(51) Int. Cl.
*A61L 33/00* (2006.01)
(52) U.S. Cl. ............ 427/2.1; 435/5; 523/107; 427/2.31; 427/430.1
(58) Field of Classification Search ...... 435/5; 523/107; 427/2.1
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,055,378 A | 10/1977 | Feneberg et al. |
| 4,113,224 A | 9/1978 | Clark et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,168,112 A | 9/1979 | Ellis et al. |
| 4,197,266 A | 4/1980 | Clark et al. |
| 4,214,014 A | 7/1980 | Höfer et al. |
| 4,287,175 A | 9/1981 | Katz |
| 4,312,575 A | 1/1982 | Peyman et al. |
| 4,321,261 A | 3/1982 | Ellis et al. |
| 4,436,730 A | 3/1984 | Ellis et al. |

(Continued)

FOREIGN PATENT DOCUMENTS

EP   0 963 761   12/1999

(Continued)

OTHER PUBLICATIONS

Lai, Yu-Chin, "The Role of Bulky Polysiloxanylalkyl Methacryates in Polyurethane-Polysiloxane Hydrogels", *Journal of Applied Polymer Science*, vol. 60, 1193-1199 (1996).

(Continued)

*Primary Examiner* — Michael Barr
*Assistant Examiner* — Andrew Bowman
(74) *Attorney, Agent, or Firm* — John E. Thomas

(57) ABSTRACT

A surface modified biomedical device is provided comprising a biomedical device having a coating on at least a portion thereof, the coating comprising a polymer or copolymer having one or more repeating units of the formula:

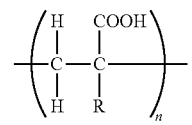

wherein R independently is a $C_2$-$C_{20}$ hydrocarbon radical and n is an integer of 2 to 5000.

11 Claims, 5 Drawing Sheets

U.S. PATENT DOCUMENTS

| | | | |
|---|---|---|---|
| 4,555,732 A | 11/1985 | Tuhro | |
| 4,632,844 A | 12/1986 | Yanagihara et al. | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Nandu et al. | |
| 5,271,876 A | 12/1993 | Ibar | |
| 5,310,779 A | 5/1994 | Lai | |
| 5,321,108 A | 6/1994 | Künzler et al. | |
| 5,358,995 A | 10/1994 | Lai et al. | |
| 5,387,662 A | 2/1995 | Künzler et al. | |
| 5,397,848 A | 3/1995 | Yang et al. | |
| 5,449,729 A | 9/1995 | Lai | |
| 5,512,205 A | 4/1996 | Lai | |
| 5,610,252 A | 3/1997 | Bambury et al. | |
| 5,616,757 A | 4/1997 | Bambury et al. | |
| 5,700,559 A | 12/1997 | Sheu et al. | |
| 5,705,583 A | 1/1998 | Bowers et al. | |
| 5,708,094 A | 1/1998 | Lai et al. | |
| 5,710,302 A | 1/1998 | Künzler et al. | |
| 5,714,557 A | 2/1998 | Künzler et al. | |
| 5,807,636 A | 9/1998 | Sheu et al. | |
| 5,908,906 A | 6/1999 | Künzler et al. | |
| 6,060,235 A * | 5/2000 | Neenan et al. | 435/5 |
| 6,428,839 B1 | 8/2002 | Künzler et al. | |
| 6,849,671 B2 * | 2/2005 | Steffen et al. | 523/107 |

FOREIGN PATENT DOCUMENTS

| | | |
|---|---|---|
| EP | 1153964 | 11/2001 |
| WO | WO 95/04609 | 2/1995 |
| WO | WO 96/31792 | 10/1996 |
| WO | WO 01/27662 | 4/2001 |

OTHER PUBLICATIONS

Ferrito et al., *Macromol. Synth.*, 11, pp. 59-62 (1992).

Chen et al., *J. Polym. Sci. Polym. Chem.*, 17, pp. 1103-1116 (1979).

* cited by examiner

SURFACE TREATMENT OF BIOMEDICAL DEVICES

BACKGROUND OF THE INVENTION

1. Technical Field

The present invention is directed to the surface treatment of biomedical devices including ophthalmic lenses, stents, implants and catheters to increase their wettability.

2. Description of Related Art

Medical devices such as ophthalmic lenses made from, for example, silicone-containing materials, have been investigated for a number of years. Such materials can generally be subdivided into two major classes, namely hydrogels and non-hydrogels. Hydrogels can absorb and retain water in an equilibrium state, whereas non-hydrogels do not absorb appreciable amounts of water. Regardless of their water content, both hydrogel and non-hydrogel silicone medical devices tend to have relatively hydrophobic, non-wettable surfaces that have a high affinity for lipids. This problem is of particular concern with contact lenses.

Those skilled in the art have long recognized the need for modifying the surface of such silicone contact lenses so that they are compatible with the eye. It is known that increased hydrophilicity of the contact lens surface improves the wettability of the contact lenses. This, in turn, is associated with improved wear comfort of contact lenses. Additionally, the surface of the lens can affect the lens's susceptibility to deposition, particularly the deposition of proteins and lipids resulting from tear fluid during lens wear. Accumulated deposition can cause eye discomfort or even inflammation. In the case of extended wear lenses (i.e., lenses used without daily removal of the lens before sleep), the surface is especially important, since extended wear lenses must be designed for high standards of comfort and biocompatibility over an extended period of time.

Silicone lenses have been subjected to plasma surface treatment to improve their surface properties, e.g., surfaces have been rendered more hydrophilic, deposit resistant, scratch-resistant, or otherwise modified. Examples of previously disclosed plasma surface treatments include subjecting the surface of a contact lens to a plasma containing an inert gas or oxygen (see, for example, U.S. Pat. Nos. 4,055,378; 4,122,942; and 4,214,014); various hydrocarbon monomers (see, for example, U.S. Pat. No. 4,143,949); and combinations of oxidizing agents and hydrocarbons such as water and ethanol (see, for example, WO 95/04609 and U.S. Pat. No. 4,632,844). U.S. Pat. No. 4,312,575 discloses a process for providing a barrier coating on a silicone or polyurethane lens by subjecting the lens to an electrical glow discharge (plasma) process conducted by first subjecting the lens to a hydrocarbon atmosphere followed by subjecting the lens to oxygen during flow discharge, thereby increasing the hydrophilicity of the lens surface.

U.S. Pat. Nos. 4,168,112, 4,321,261 and 4,436,730 disclose methods for treating a charged contact lens surface with an oppositely charged ionic polymer to form a polyelectrolyte complex on the lens surface that improves wettability.

U.S. Pat. No. 4,287,175 discloses a method of wetting a contact lens that comprises inserting a water-soluble solid polymer into the cul-de-sac of the eye. The disclosed polymers include cellulose derivatives, acrylates and natural products such as gelatin, pectins and starch derivatives.

U.S. Pat. No. 5,397,848 discloses a method of incorporating hydrophilic constituents into silicone polymer materials for use in contact and intra-ocular lenses.

U.S. Pat. Nos. 5,700,559 and 5,807,636 disclose hydrophilic articles (e.g., contact lenses) comprising a substrate, an ionic polymeric layer on the substrate and a disordered polyelectrolyte coating ionically bonded to the polymeric layer.

U.S. Pat. No. 5,705,583 discloses biocompatible polymeric surface coatings. The polymeric surface coatings disclosed include coatings synthesized from monomers bearing a center of positive charge, including cationic and zwitterionic monomers.

European Patent Application No. EP 0 963 761 A1 discloses biomedical devices with coatings that are said to be stable, hydrophilic and antimicrobial, and which are formed using a coupling agent to bond a carboxyl-containing hydrophilic coating to the surface of the devices by ester or amide linkages.

U.S. Pat. No. 6,428,839 discloses a method for improving the wettability of a medical device which includes the steps of (a) providing a medical device formed from a monomer mixture comprising a hydrophilic monomer and a silicone-containing monomer; and (b) contacting a surface of the medical device with a solution including a polymer or copolymer of (meth)acrylic acid.

Typically, a medical device such as a contact lens is exposed to an aqueous environment having a pH in the range from 6.5 to 8.0 during storage in a package and during wear. A problem associated with coatings formed from a polymer or copolymer of (meth)acrylic acid is that during use of the contact lens in this pH environment, these polymers are highly ionized and have little surface activity. Therefore, the coating can be removed from the lens relatively easily thereby exposing the lens surface and resulting in a reduction in wetting and lubricity.

Accordingly, it would be desirable to provide improved biomedical devices such as a silicone hydrogel contact lens with an optically clear, hydrophilic surface film that will not only exhibit improved wettability, but which will generally allow the use of a silicone hydrogel contact lens in the human eye for an extended period of time. In the case of a silicone hydrogel lens for extended wear, it would be desirable to provide a contact lens with a surface that is also highly permeable to oxygen and water. Such a surface treated lens would be comfortable to wear in actual use and would allow for the extended wear of the lens without irritation or other adverse effects to the cornea.

SUMMARY OF THE INVENTION

In accordance with one embodiment of the present invention, a method for improving the wettability of a biomedical device is provided comprising the step of contacting a surface of the biomedical device with a composition comprising a polymer or copolymer having one or more repeating units of the formula:

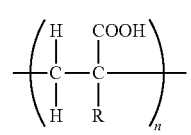

wherein R independently is a $C_2$-$C_{20}$ hydrocarbon radical and n is an integer of 2 to 5000.

In accordance with a second embodiment of the present invention, a method for improving the wettability of a biomedical device is provided comprising the step of contacting a surface of a biomedical device formed from a monomeric mixture comprising a hydrophilic monomer and a silicone-containing monomer with a composition comprising a polymer or copolymer having one or more repeating units of the formula:

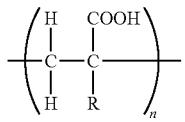

wherein R independently is a $C_2$-$C_{20}$ hydrocarbon radical and n is an integer of 2 to 5000.

In accordance with a third embodiment of the present invention, a surface modified biomedical device is provided comprising a biomedical device having a coating on a surface thereof, the coating comprising a polymer or copolymer having one or more repeating units of the formula:

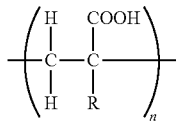

wherein R independently is a $C_2$-$C_{20}$ hydrocarbon radical and n is an integer of 2 to 5000.

In accordance with a fourth embodiment of the present invention, a surface modified biomedical device is provided comprising a biomedical device having a coating on a surface thereof, the coating comprising a polymer or copolymer obtained from the polymerization or copolymerization of a monomeric mixture comprising one or more $C_2$-$C_{20}$ straight chain, branched, and cyclic 2-alpha-alkyl acrylic acids.

In accordance with a fifth embodiment of the present invention, a method of forming a surface modified biomedical device is provided comprising (a) providing a biomedical device; and (b) coating a surface of the biomedical device with a coating composition comprising a polymer or copolymer having one or more repeating units of the formula:

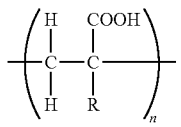

wherein R independently is a $C_2$-$C_{20}$ hydrocarbon radical and n is an integer of 2 to 5000.

In accordance with a sixth embodiment of the present invention, a method is provided comprising:
(a) immersing an ophthalmic device in a solution comprising a polymer or copolymer having one or more repeating units of the formula:

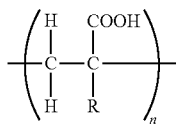

wherein R independently is a $C_2$-$C_{20}$ hydrocarbon radical and n is an integer of 2 to 5000, wherein the solution has an osmolality of at least about 200 mOsm/kg and a pH in the range of about 6 to about 9;

(b) packaging the solution and the device in a manner preventing contamination of the device by microorganisms; and
(c) sterilizing the packaged solution and device.

In accordance with a seventh embodiment of the present invention, a packaging system for the storage of an ophthalmic device is provided comprising a sealed container containing one or more unused ophthalmic devices immersed in an aqueous packaging solution comprising a polymer or copolymer having one or more repeating units of the formula:

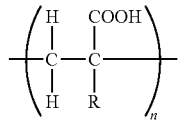

wherein R independently is a $C_2$-$C_{20}$ hydrocarbon radical and n is an integer of 2 to 5000, wherein the solution has an osmolality of at least about 200 mOsm/kg and a pH in the range of about 6 to about 9 and is heat sterilized.

In accordance with an eighth embodiment of the present invention, a packaging system for the storage of an ophthalmic device is provided comprising:
(a) an aqueous packaging solution comprising a polymer or copolymer having one or more repeating units of the formula:

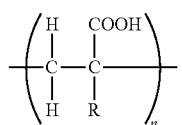

wherein R independently is a $C_2$-$C_{20}$ hydrocarbon radical and n is an integer of 2 to 5000, wherein the solution has an osmolality of at least about 200 mOsm/kg and a pH in the range of about 6 to about 9;
(b) at least one ophthalmic device; and
(c) a container for holding the solution and ophthalmic device sufficient to preserve the sterility of the solution and ophthalmic device, wherein the solution does not contain an effective disinfecting amount of a disinfecting agent.

DETAILED DESCRIPTION OF THE PREFERRED EMBODIMENTS

Figure 1:
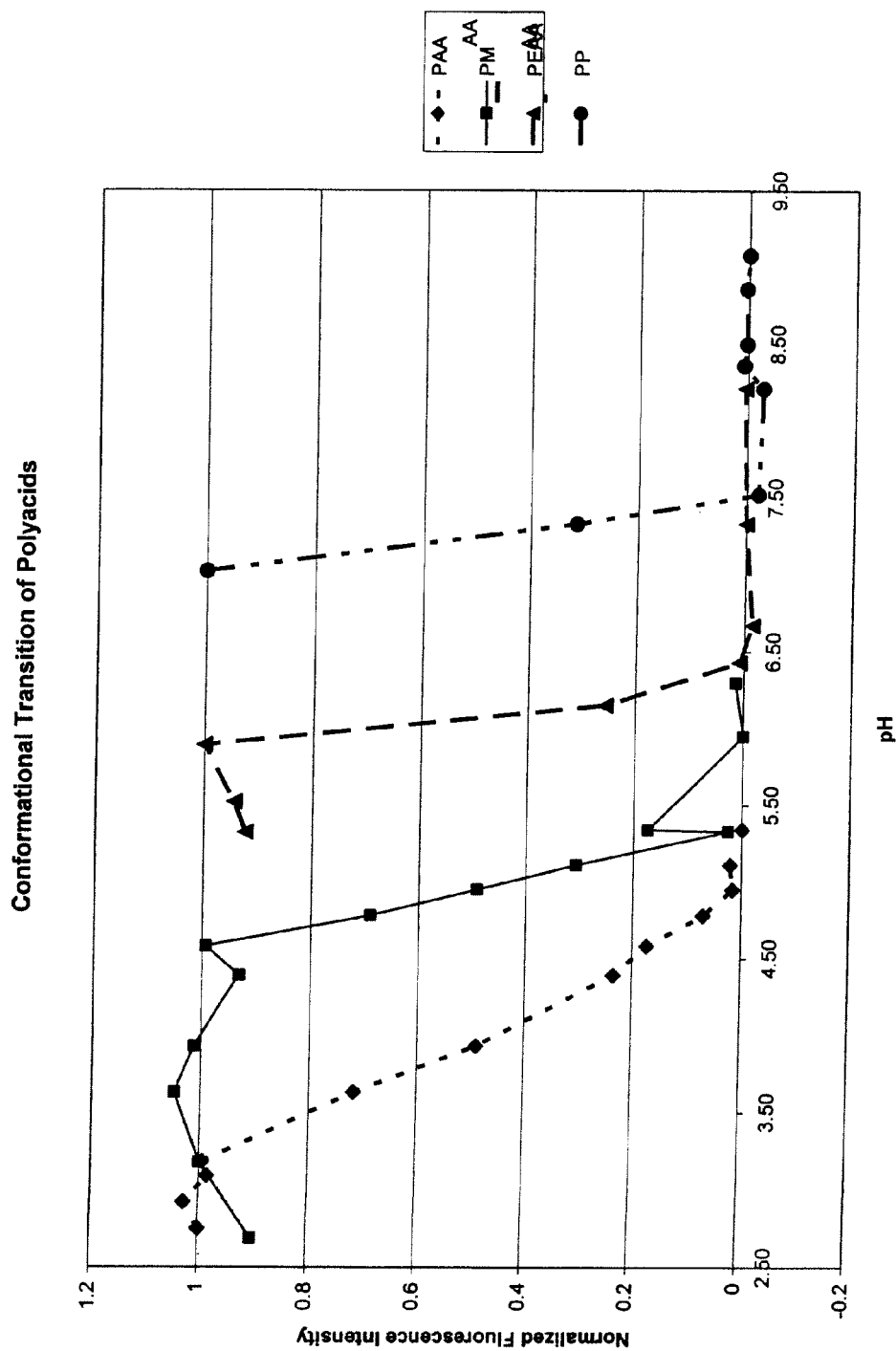
FIG. 1 is a graphical representation showing the conformational transition of the substituent group at the 2-position of a series of poly(carboxylic acid)s.

The present invention provides a surface modified biomedical device such as a contact lens, e.g., a silicone hydrogel contact lens, which has a coating on at least a portion thereon. The coating composition advantageously improves the hydrophilicity and lipid resistance of the biomedical device by forming a coating thereon.

The preferred biomedical devices for use herein are ophthalmic devices, more preferably contact lenses, and most preferably contact lenses made from silicone hydrogels. The biomedical devices such as wettable silicone-based hydrogel formulations are coated with the coating composition described herein to render a lubricious, stable, highly wettable poly(carboxylic acid) containing surface coating on the biomedical device.

As used herein, the terms "lens" and "opthalmic device" refer to devices that reside in or on the eye. These devices can provide optical correction, wound care, drug delivery, diagnostic functionality or cosmetic enhancement or any combination of these properties. Representative examples of such devices include, but are not limited to, soft contact lenses, e.g., soft, hydrogel lens, soft, non-hydrogel lens and the like, hard contact lenses, e.g., hard, gas permeable lens materials and the like, intraocular lenses, overlay lenses, ocular inserts, optical inserts and the like. As is understood by one skilled in the art, a lens is considered to be "soft" if it can be folded back upon itself without breaking. Any material known to produce a biomedical device including an ophthalmic device can be used herein.

It is particularly useful to employ biocompatible materials herein including both soft and rigid materials commonly used for opthalmic lenses, including contact lenses. The preferred substrates are hydrogel materials, including silicone hydrogel materials. Particularly preferred materials include vinyl functionalized polydimethylsiloxanes copolymerized with hydrophilic monomers as well as fluorinated methacrylates and methacrylate functionalized fluorinated polyethylene oxides copolymerized with hydrophilic monomers. Representative examples of substrate materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

A wide variety of materials can be used herein, and silicone hydrogel contact lens materials are particularly preferred. Hydrogels in general are a well known class of materials that comprise hydrated, cross-linked polymeric systems containing water in an equilibrium state. Silicone hydrogels generally have a water content greater than about 5 weight percent and more commonly between about 10 to about 80 weight percent. Such materials are usually prepared by polymerizing a mixture containing at least one silicone-containing monomer and at least one hydrophilic monomer. Typically, either the silicone-containing monomer or the hydrophilic monomer functions as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Representative examples of applicable silicon—containing monomeric units include bulky polysiloxanylalkyl(meth) acrylic monomers. An example of a bulky polysiloxanylalkyl (meth)acrylic monomer is represented by the structure of Formula I:

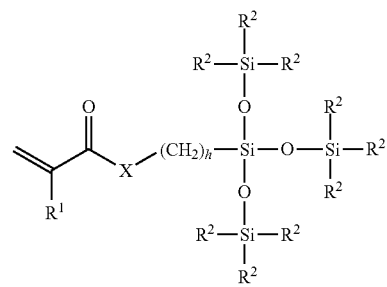

wherein X denotes —O— or —NR—; each $R^1$ independently denotes hydrogen or methyl; each $R^2$ independently denotes a lower alkyl radical, phenyl radical or a group represented by

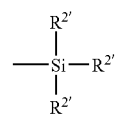

wherein each $R^{2'}$ independently denotes a lower alkyl or phenyl radical; and h is 1 to 10.

Examples of bulky monomers are methacryloxypropyl tris (trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris (trimethylsiloxy)silyl]propyl vinyl carbamate; 3-[tris (trimethylsiloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

$$E(*D*A*D*G)_a *D*A*D*E'; \text{ or} \qquad (II)$$

$$E(*D*G*D*A)_a *D*A*D*E'; \text{ or} \qquad (III)$$

wherein:
D independently denotes an alkyl diradical, an alkyl cycloalkyl diradical, a cycloalkyl diradical, an aryl diradical or an alkylaryl diradical having 6 to about 30 carbon atoms;
G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;
* denotes a urethane or ureido linkage;
a is at least 1;
A independently denotes a divalent polymeric radical of Formula IV:

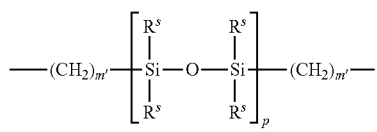

(IV)

wherein each $R^5$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;
each of E and E' independently denotes a polymerizable unsaturated organic radical represented by Formula V:

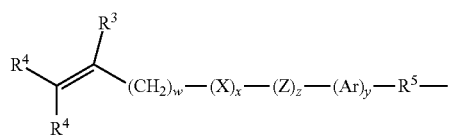

(V)

wherein: $R^3$ is hydrogen or methyl;
$R^4$ is hydrogen, an alkyl radical having 1 to 6 carbon atoms, or a —CO—Y—$R^6$ radical wherein Y is —O—, —S— or —NH—;
$R^5$ is a divalent alkylene radical having 1 to about 10 carbon atoms;
$R^6$ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.
A preferred silicone-containing urethane monomer is represented by Formula VI:

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

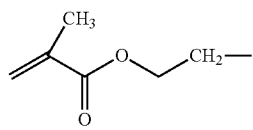

In another embodiment of the present invention, a silicone hydrogel material comprises (in bulk, that is, in the monomer mixture that is copolymerized) about 5 to about 50 percent, and preferably about 10 to about 25, by weight of one or more silicone macromonomers, about 5 to about 75 percent, and preferably about 30 to about 60 percent, by weight of one or more polysiloxanylalkyl (meth)acrylic monomers, and about 10 to about 50 percent, and preferably about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the invention. The silane macromonomer may be a silicon-containing vinyl carbonate or vinyl carbamate or a polyurethane-polysiloxane having one or more hard-soft-hard blocks and end-capped with a hydrophilic monomer.

Suitable hydrophilic monomers include, but are not limited to, amides such as dimethylacrylamide and dimethylmethacrylamide, cyclic lactams such as N-vinyl-2-pyrrolidone and poly(alkene glycols) functionalized with polymerizable groups. Examples of useful functionalized poly(alkene glycols) include poly(diethylene glycols) of varying chain length containing monomethacrylate or dimethacrylate end caps. In one embodiment, the poly(alkene glycol) polymer can contain at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Another class of representative silicone-containing monomers includes fluorinated monomers. Such monomers have been used in the formation of fluorosilicone hydrogels to reduce the accumulation of deposits on contact lenses made

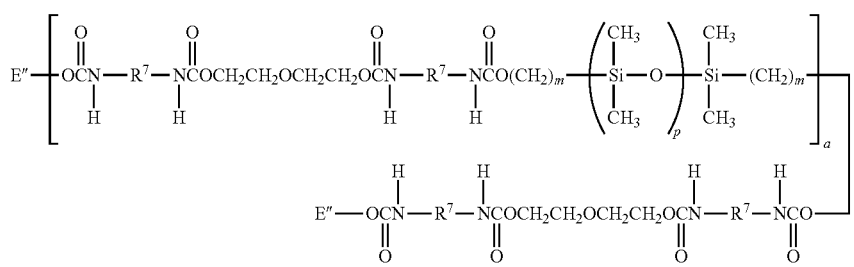

therefrom, as disclosed in, for example, U.S. Pat. Nos. 4,954, 587; 5,010,141 and 5,079,319. The use of silicone-containing monomers having certain fluorinated side groups, i.e., —(CF$_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates that can benefit by being coated with the hydrophilic coating composition according to the present invention and have been disclosed in various publications and are being continuously developed for use in contact lenses and other medical devices can also be used.

Contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

Typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product is of particular importance for silicone hydrogels, primarily due to the inclusion of silicone-containing monomers which may tend to separate from the hydrophilic comonomer. Suitable organic diluents include, for example, monohydric alcohols such as $C_6$-$C_{10}$ straight-chained aliphatic monohydric alcohols, e.g., n-hexanol and n-nonanol; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure. Generally, the diluent may be included at about 5 to about 60 percent by weight of the monomeric mixture, with about 10 to about 50 percent by weight being especially preferred. If necessary, the cured lens may be subjected to solvent removal, which can be accomplished by evaporation at or near ambient pressure or under vacuum. An elevated temperature can be employed to shorten the time necessary to evaporate the diluent.

Following removal of the organic diluent, the lens can then be subjected to mold release and optional machining operations. The machining step includes, for example, buffing or polishing a lens edge and/or surface. Generally, such machining processes may be performed before or after the article is released from a mold part. As an example, the lens may be dry released from the mold by employing vacuum tweezers to lift the lens from the mold.

Next, the biomedical devices are contacted with a coating composition of this invention. The devices may either be unhydrated or prehydrated in water or aqueous solution. The coating composition of this invention contains a polymer or copolymer having one or more repeating units of the formula:

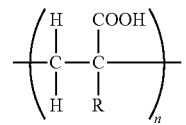

wherein R independently is a $C_2$-$C_{20}$ hydrocarbon radical and preferably a $C_2$-$C_6$ hydrocarbon radical and n is an integer of 2 to 5000, preferably 2 to about 2000 and most preferably from about 10 to about 1000. Suitable $C_2$-$C_{20}$ hydrocarbon radicals include, by way of example, straight chain or branched alkyl groups, cycloalkyl groups, cycloalkyl alkyl groups, cycloalkenyl groups, aryl groups, arylalkyl groups and the like. The copolymers can be random, block or grafted copolymers. The polymers or copolymers can have a weight average molecular weight ranging from about 500 to about 1,000,000 and preferably from about 10,000 to about 500,000.

Representative examples of alkyl groups for use herein include, by way of example, a straight or branched hydrocarbon chain radical containing carbon and hydrogen atoms of from 2 to 20 and preferably 2 to 6 carbon atoms with or without unsaturation, to the rest of the molecule, e.g., ethyl, propyl, 1-methylethyl (isopropyl), n-butyl, n-pentyl, etc., and the like.

Representative examples of cycloalkyl groups for use herein include, by way of example, a substituted or unsubstituted non-aromatic mono or multicyclic ring system of from 3 to 20 and preferably about 3 to about 6 carbon atoms such as, for example, cyclopropyl, cyclobutyl, cyclopentyl, cyclohexyl, and the like.

Representative examples of cycloalkylalkyl groups for use herein include, by way of example, a substituted or unsubstituted cyclic ring-containing radical containing from from 3 to 20 and preferably about 3 to 6 carbon atoms directly attached to an alkyl group which is then attached to the main structure of the monomer at any carbon from the alkyl group that results in the creation of a stable structure such as, for example, cyclopropylmethyl, cyclobutylethyl, and the like.

Representative examples of cycloalkenyl groups for use herein include, by way of example, a substituted or unsubstituted cyclic ring-containing radical containing from from 3 to 20 and preferably about 3 to 6 carbon atoms with at least one carbon-carbon double bond such as, for example, cyclopropenyl, cyclobutenyl, cyclopentenyl and the like.

Representative examples of aryl groups for use herein include, by way of example, a substituted or unsubstituted aromatic-containing radical having from 5 to 20 and preferably 5 to 7 carbon atoms such as, for example, phenyl, and the like.

Representative examples of arylalkyl groups for use herein include, by way of example, a substituted or unsubstituted aryl group as defined above directly bonded to an alkyl group as defined above, e.g., —$CH_2C_6H_5$, —$C_2H_5C_6H_5$ and the like.

In general, the polymer or copolymer can be obtained from the polymerization or copolymerization of a monomeric mixture comprising one or more $C_2$-$C_{20}$ 2-alpha-hydrocarbon susbstituted acrylic acids. Preferred hydrocarbon susbstituted acrylic acid monomers for use in preparing the polymeric materials include ethylacrylic acid (EAA), propylacrylic acid (PAA), butylacrylic acid (BAA) and mixtures thereof.

Copolymers of these monomers by themselves or other monomers such as acrylic acid can be used. Representative examples of additional monomers include hydrophilic monomers such as acrylamides, e.g., N,N-dimethylacrylamide (DMA) and the like; vinyl lactams, e.g., N-vinylpyrrolidinone (NVP) and the like; (meth)acrylated poly(alkylene oxides), e.g., methoxypolyoxyethylene methacrylates and the like, hydroxyalkyl (meth)acrylates, e.g., hydroxyethyl methacrylate (HEMA) and the like, epoxy-functional monomers, e.g., glycidyl methacrylate (GMA) and the like and mixtures thereof.

The polymers or copolymers can be synthesized in any manner known per se, from the corresponding monomers (the term monomer herein also including a macromer) by a polymerization reaction customary to the person skilled in the art. For example, in one embodiment, the polymers or copolymers can be obtained by at least (a) mixing the one or more monomers together; (b) adding a polymerization initiator; (c) subjecting the monomer/initiator mixture to thermal energy or a source of ultraviolet or other light and curing the mixture. Typical polymerization initiators include free-radical-generating polymerization initiators of the type illustrated by acetyl peroxide, lauroyl peroxide, decanoyl peroxide, coprylyl peroxide, benzoyl peroxide, tertiary butyl peroxypivalate, sodium percarbonate, tertiary butyl peroctoate, and azobis-isobutyronitrile (AIBN). Ultraviolet free-radical initiators illustrated by diethoxyacetophenone can also be used. The curing process will of course depend upon the initiator used and the physical characteristics of the comonomer mixture such as viscosity. In any event, the level of initiator employed may vary within the range of about 0.01 to about 2 weight percent of the mixture of monomers. Usually, a mixture of the above-mentioned monomers is warmed with addition of a free-radical former.

In an alternative embodiment, block copolymers can be synthesized by controlled free radical techniques known in the art to produce a segmented block copolymer.

Polymerization of the monomeric mixture to form the polymers or copolymers can be carried out in the presence of a solvent. Suitable solvents are in principle all solvents which dissolve the monomeric mixture used such as, for example, water, alcohols such as lower alkanols, e.g., methanol, methanol and the like; carboxamides such as dimethylformamide and the like; dipolar aprotic solvents such as dimethyl sulfoxide and the like; ketones such as acetone, methyl ethyl ketone, cyclohexanone, and the like; aliphatic or aromatic hydrocarbons such as toluene, xylene, n-hexane and the like; ethers such as THF, dimethoxyethane, dioxane and the like; halogenated hydrocarbons such as trichloroethane and the like, and also mixtures of suitable solvents, for example mixtures of water and an alcohol, e.g., a water/methanol or water/ethanol mixture, and the like.

The coating can be formed on the biomedical device by conventional techniques, for example, immersion, dip coating, spray coating, electrostatic coating and the like. For example, in one embodiment, a surface of a biomedical device can be contacted with a coating composition of this invention containing a polymer or copolymer formed from a monomeric mixture containing at least one $C_2$-$C_{20}$ hydrocarbon substituted acrylic acid monomer, and the polymer or copolymer forms a coating on the surface thereof. The biomedical device can be contacted with the coating polymer in an aqueous or organic solvent at a temperature and time period sufficient to form the coating on the surface of the device.

Alternatively, a biomedical device such as a contact lens can be coated by immersing the biomedical device in a packaging solution containing the polymer or copolymers described hereinabove. In one embodiment, the solution is a packaging solution for storing the lens. The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations. The polymer or copolymer will ordinarily be present in the solution in an amount ranging from about 10 ppm to about 10 wt. %, and preferably about 0.1 wt. % to about 5 wt. %.

The solution of the present invention should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions should be maintained within the range of about 6 to about 9, and preferably about 6.5 to about 7.8. Suitable buffers may be added, such as boric acid, sodium borate, potassium citrate, citric acid, sodium bicarbonate, trimethamine, and various mixed phosphate buffers (including combinations of $Na_2 HPO_4$, $NaH_2 PO_4$ and $KH2 PO_4$) and mixtures thereof. Generally, buffers will be used in amounts ranging from about 0.05 to about 2.5 percent by weight, and preferably from about 0.1 to about 1.5 percent by weight of the solution.

Typically, the solutions of the present invention are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to, sodium and potassium chloride, dextrose, glycerin, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, preferably from about 200 to about 400 mOsm/kg, more preferably from about 250 to about 350 mOsm/kg, and most preferably from about 280 to about 320 mOsm/kg.

If desired, one or more additional components can be included in the packaging solution. Such additional component or components are chosen to impart or provide at least one beneficial or desired property to the packaging solution.

Such additional components may be selected from components which are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetraacetate, alkali metal hexametaphosphate, citric acid, sodium citrate and the like and mixtures thereof.

Useful viscosity builders include, but are not limited to, hydroxyethyl cellulose, hydroxymethyl cellulose, polyvinyl pyrrolidone, polyvinyl alcohol and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing a biomedical device such as an ophthalmic lens according to the present invention includes at least packaging an ophthalmic lens immersed in an aqueous ophthalmic-lens packaging solution. The method may include immersing the lens in an aqueous packaging solution prior to delivery to the customer/wearer, directly following manufacture of the ophthalmic lens. Alternately, the packaging and storing in the solution of the present invention may occur at an intermediate point before delivery to the ultimate customer (wearer) but following manufacture and transportation of the lens in a dry state, wherein the dry lens is hydrated by immersing the lens in the ophthalmic-lens packaging solution. Consequently, a package for delivery to a customer may include a sealed container containing one or more unused ophthalmic lenses immersed in an aqueous packaging solution according to the present invention.

In one embodiment, the steps leading to the present ophthalmic lens packaging system includes (1) molding an ophthalmic lens in a mold comprising a posterior and anterior mold portion, (2) removing the lens from the mold and hydrating the lens, (3) introducing the packaging solution with the $C_2$-$C_{20}$ hydrocarbon substituted acrylic acid polymer or copolymer into the container with the lens supported therein, and (4) sealing the container. Preferably, the method also includes the step of sterilizing the contents of the container. Sterilization may take place prior to, or most conveniently after, sealing of the container and may be effected by any suitable method known in the art, e.g., by autoclaving of the sealed container and its contents at temperatures of about 120° C. or higher.

In another embodiment, this invention comprises: (1) molding an ophthalmic lens in a mold comprising a posterior and anterior mold portion, (2) removing the lens from the mold, and (3) introducing the lens and the solution with the $C_2$-$C_{20}$ hydrocarbon substituted acrylic acid polymer or copolymer into a container.

The following examples are provided to enable one skilled in the art to practice the invention and are merely illustrative of the invention. The examples should not be read as limiting the scope of the invention as defined in the claims.

EXAMPLE 1

Step I: Preparation of 2-Ethylacrylic acid.

2-Ethylacrylic acid was prepared from diethyl ethylmalonate using procedures set forth in the literature (e.g., Ferrito et al., *Macromol. Synth.*, 11, pp. 59-62 (1992)). Diethyl ethylmalonate (100 g, 0.53 mol) was added to a 1 L round bottom flask and stirred overnight with 700 mL of 1 M KOH in 95% ethanol. The ethanol was then removed with a rotary evaporator and the residue was dissolved in a minimum amount of water and acidified to a pH of 2.0 by slow addition of concentrated HCl. The separated oil (2-carboethoxybutyric acid) was taken up into diethyl ether (3×200 mL portions of ether in a separatory funnel), dried over magnesium sulfate and concentrated on a rotary evaporator. The crude 2-carboethoxybutyric acid (84.9 g, 0.53 mol) was placed in a 1 L round bottom flask and cooled to −5° C. Diethylamine (55 mL, 0.53 mol) was then added to the flask and an addition funnel containing 43.5 g formaline solution (0.54 mol) was added dropwise to the reaction mixture while allowing the solution to slowly warm to room temperature. After stirring for 24 hours, the addition funnel was replaced with a reflux condenser and the reaction was warmed to 60° C. for 8 hours. The reaction mixture was then cooled to 0° C. and concentrated sulfuric acid was added slowly until evolution of gas ceases. The mixture was extracted with three 200 mL portions of diethyl ether, dried over magnesium sulfate, and concentrated on a rotary evaporator to obtain 2-ethylacrylate. Crude 2-ethylacrylate (64.1 g, 0.5 mol) was placed in a 1 L round bottom flask and 600 ml of 2M aqueous KOH was added. The flask was fitted with a reflux condenser and the reaction was refluxed for 20 hours. The solution was allowed to cool to room temperature and was acidified with 1N HCl to a pH of 2. The separated oil was extracted four times with 700 mL of ether, dried over magnesium sulfate and concentrated on a rotary evaporator. The yellow oil was vacuum distilled (bp 50° C./1 mm Hg) to yield pure, colorless 2-ethylacrylic acid (35 g).

Step II: Preparation of Poly(2-ethylacrylic acid).

Distilled 2-ethylacrylic acid was placed in ampules and subjected to four freeze-degas-thaw cycles and sealed under vacuum. AIBN (from 0.1-5 mol %) was added and the polymerizations was carried out in bulk at 64° C. for 24 hours. The resulting slurry was dissolved in methanol and precipitated into diethyl ether. The precipitated polymer was collected by filtration, dissolved in pH 9 phosphate buffer, and dialyzed against water for several days in cellulose dialysis tubing (MWCO=1000).

EXAMPLE 2

Step I: Preparation of 2-Propylacrylic acid.

2-Propylacrylic acid was prepared from diethyl propylmalonate by a modification of a procedure set forth in the literature (e.g., Ferrito et al., *Macromol. Synth.*, 11, pp. 59-62 (1992)) in which diethyl propylmalonate was used instead of diethyl ethylmalonate. The procedure used was identical to that set forth in Example 1. Crude 2-propylacrylic acid (yellow oil) was vacuum distilled (b.p. 60° C./1 mm Hg) to yield pure, colorless 2-Propylacrylic acid (35 gm).

Step II: Preparation of Poly(2-propylacrylic acid).

Distilled 2-Propylacrylic acid was placed in ampules and subjected to four freeze-degas-thaw cycles and sealed under vacuum. AIBN (from 0.1-5 mol %) was added and the polymerizations were carried out in bulk at 64° C. for 24 hours. The resulting slurry was dissolved in methanol and precipitated into diethyl ether. The precipitated polymer was collected by filtration, dissolved in pH 10 phosphate buffer, and dialyzed against water for several days in cellulose dialysis tubing (MWCO=1000).

EXAMPLE 3

Conformational Properties of Poly(carboxylic acid)s.

The conformational transition of a series of poly(carboxylic acid)s in solution was studied by observing the steady-state fluorescence of codissolved pyrene using procedures set forth in the literature (e.g., Chen et al., *J. Polym. Sci. Polym. Chem.*, 17, pp. 1103-1116 (1979)). In this study, a polymer stock solution of low buffer capacity was prepared by dissolving the poly(carboxylic acid) (4 mg/ml) and pyrene (200 µM) in a 5 mM buffer (phosphate or borate) of high enough pH for dissolution. Buffers of higher buffer capacity (100 mM) were prepared ranging in pH from 2.2 to 10.0 using either citric acid-phosphate, sodium and disodium phosphate, or boric acid-borax buffering systems. Samples for fluorescence measurements were prepared by mixing 0.5 ml of the polymer/pyrene stock solution with 1.5 ml of the higher buffer capacity solutions at various solution pH, to give final concentrations of 1 mg/mL of the poly(carboxylic acid) and 50 µM pyrene. Pyrene was excited at 337 nm and the conformational transition was followed by measuring the intensity of the fluorescence emitted at 373 nm (peak 1) and at 384 nm (peak 3) using a PTI fluorescence spectrophotometer.

The series of poly(carboxylic acid)s studied were polyacrylic acid (PAA, MW=450,000, available from Polysciences, Inc., Warrington, Pa.), poly(methacrylic acid) (PMAA, MW=9,500 available from Aldrich Chemical, Milwaukee, Wis.], poly(2-ethylacrylic acid) (PEAA, MW=30,000) of Example 1, and poly(2-propylacrylic acid) (PPAA, MW=9,000) of Example 2. In this series of poly(carboxylic acid)s, the substituent at the 2 position progressively becomes more hydrophobic going from a proton, to a methyl group, to an ethyl group, to a propyl group. The results of the conformational transition study show the effect of the substituent group on the conformational transition can be seen in FIG. 1. For PAA, the transition midpoint is approximately at a pH of 4, and this transition midpoint shifts to higher pH's for the more hydrophobically modified poly(carboxylic acid)s [PMAA=pH 5; PEAA=pH 6.25; and PPAA=pH 7.25]. This conformational transition can be correlated with the ionization of the polymer where at higher pH's the chains are highly ionized and more hydrophilic (therefore showing a low fluorescence intensity in the pyrene assay) and at lower pH's the carboxylate groups along the polymer chain become protonated and the polymer chain collapsed to a more compact coil, is more hydrophobic, and therefore more surface active as well. This situation corresponds to the high fluorescence intensity in the pyrene assay, where the pyrene is localized in the hydrophobic collapsed coil.

EXAMPLE 4

Treatment of Contact Lenses with Polyacid solutions.

Aqueous solutions containing the PAA, PMAA, PEAA, and PPAA described in Example 3 were prepared at a concentration of 0.5% by weight and the pH's were adjusted to 2.9, 3.2, 5.5, and 6.1 respectively. PureVision® contact lenses (Bausch & Lomb Incorporated, Rochester, N.Y., USA) made of balafilcon A were rinsed in deionized water and placed in a lens vial along with 2.5 mL of the aforementioned aqueous solutions. The lens vials were then autoclaved for 30 minutes (121° C., 30 PSI). After cooling, the lenses were removed from the autoclave vials, rinsed by dipping into deionized water 10 times and placed in buffers of varying pH (2.6-8.8) in scintillation vials. After thorough rinsing of the lenses at desired pH, the lenses were subjected to surface analysis. Alternatively, the lenses and solutions of this invention could be autoclaved while contained in a blister package sealed with lidstock.

EXAMPLE 5

XPS Analysis of coated lenses.

Figure 2:
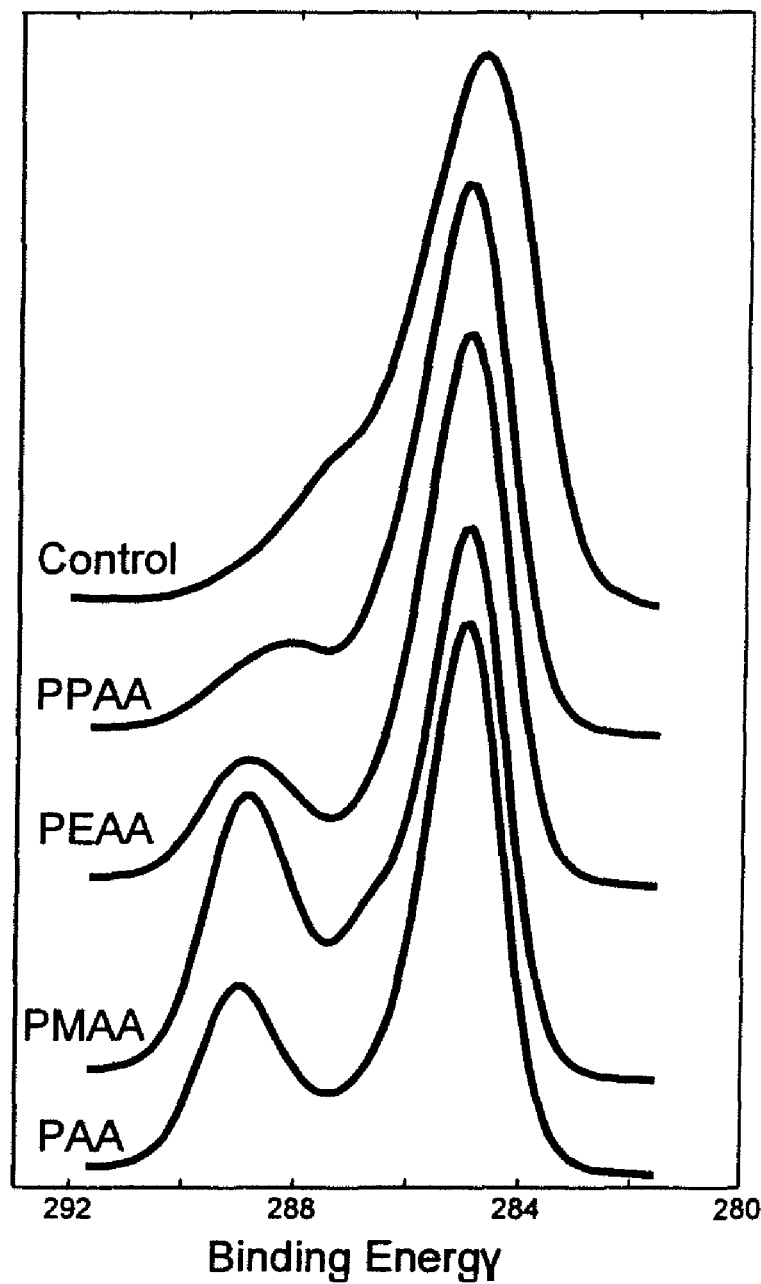
FIG. 2 is a graphical representation showing the Carbon 1s (C1s) photoelectron region of the X-ray Photoelectron Spectrometer (XPS) spectra of a series of poly(carboxylic acid)s.
Figure 3:
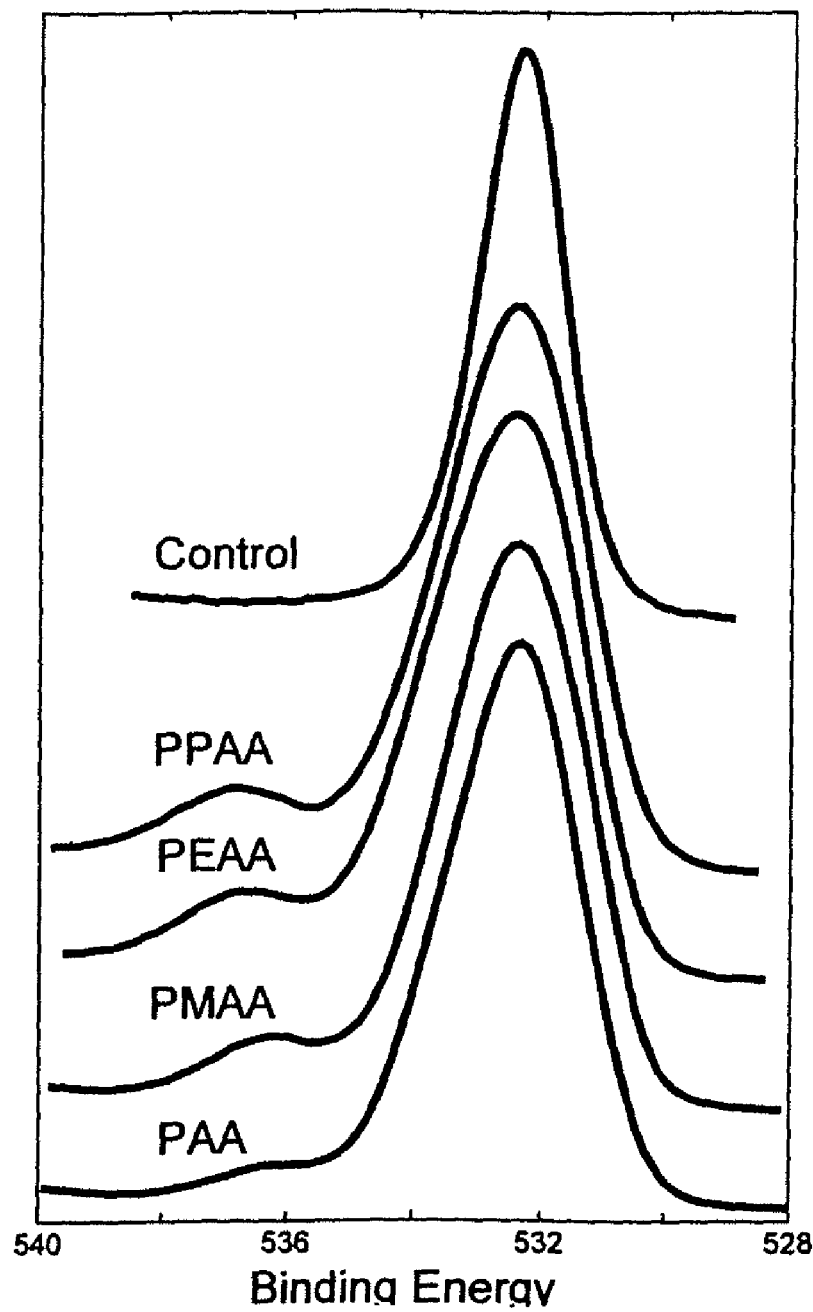
FIG. 3 is a graphical representation showing the Oxygen 1s (O1s) photoelectron region of the XPS spectra of a series of different poly(carboxylic acid)s.

The PureVision® lenses treated with the four different poly(carboxylic acid)s [PAA, PMAA, PEAA, and PPAA] and thoroughly rinsed with varying pH buffers (2.6-8.8) of Example 4 were analyzed using XPS. Three sections from both the anterior surface (side of lens facing air) and the posterior surface (side of lens in contact with eye) were analyzed. The results are summarized in FIGS. 2-4, which show the Carbon 1s (C1s) photoelectron region, the Oxygen 1s (O1s) photoelectron region, and the percent silicone concentration in the XPS spectra, respectively. In FIG. 2, the carbonyl carbon can be seen in the carbon 1s region of the XPS spectra at around 289 eV. This peak appears to be strongest for PAA and PMA, and weaker as you go to PEAA and PPAA which is expected since the number of carbons in the repeat unit of the poly(carboxylic acid) increases as you go from PMAA (4) to PEAA (5) to PPAA (6). In FIG. 3, the oxygen 1s region of the XPS spectra is shown. The peak that appears at around 537 eV can be attributed to the —OH group of the carboxylic acid on the polyacids.

Figure 4:
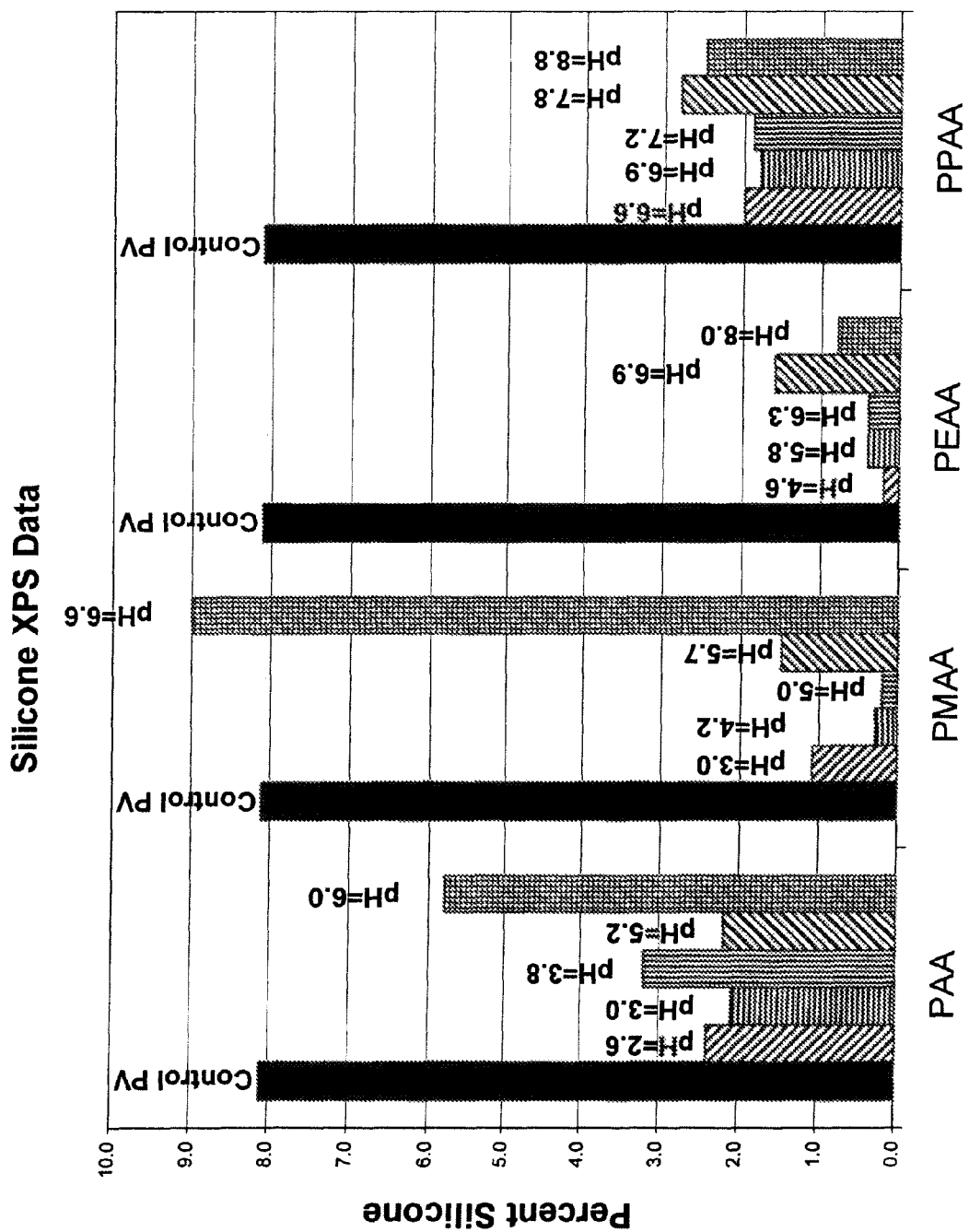
FIG. 4 is a graphical representation showing the percent silicone concentration of the XPS spectra of a series of poly(carboxylic acid)s.

FIG. 4 shows the percent silicone in the XPS spectra of PureVision® lenses treated with the various poly(carboxylic acid)s that have been thoroughly rinsed with buffers of various pH's after being autoclaved in the polyacid solutions. The pH of the rinsing solution is noted in the figure above each of the bars. The PureVision control is shown as solid black bars. One can easily see that by examination of the percent silicone in the XPS spectra that the PAA coating begins to rinse away from the substrate at a pH of 6.0, PMAA begins to rinse away from the substrate at a pH of 6.6, while the PEAA and PPAA remain strongly bonded to the surface at pH's of 8.0 and 8.8 respectively. This data demonstrates that the more hydrophobically modified poly(carboxylic acid)s, i.e., PEAA and PPAA, are more difficult to rinse away from the underlying lens substrates and are capable of covering the silicone surface at pH ranges most desirable for a lens packaging solution (pH's of 6.7-8.0).

EXAMPLE 7

Contact Angle Analysis of Coated Lenses

Contact angle analysis was done on twenty lots of poly (carboxylic acid) coated lenses and one lot of control PureVision® lenses. The test lenses were coated with PAA, PMAA, PEAA, or PPAA described in Example 3 at five different pH values for each coating. The lenses were removed from the buffer solution and quartered using a clean scalpel. The quarters were mounted on a clean glass slide and dried overnight in a nitrogen dry-box. Contact angles were measured on the dehydrated lenses at two points on each quarter. The instrument used for measurement was an AST Products Video Contact Angle System (VCA) 2500XE. This instrument utilizes a low-power microscope that produces a sharply defined image of the water drop, which is captured immediately on the computer screen. HPLC water was drawn into the VCA system microsyringe, and a 0.6 µl drop is dispensed from the syringe onto the sample. The contact angle was calculated by placing three to five markers along the circumference of the drop. The software calculates a curve representing the circumference of the drop and the contact angle was recorded. Both a right and left contact angle were reported for each measurement.

Figure 5:
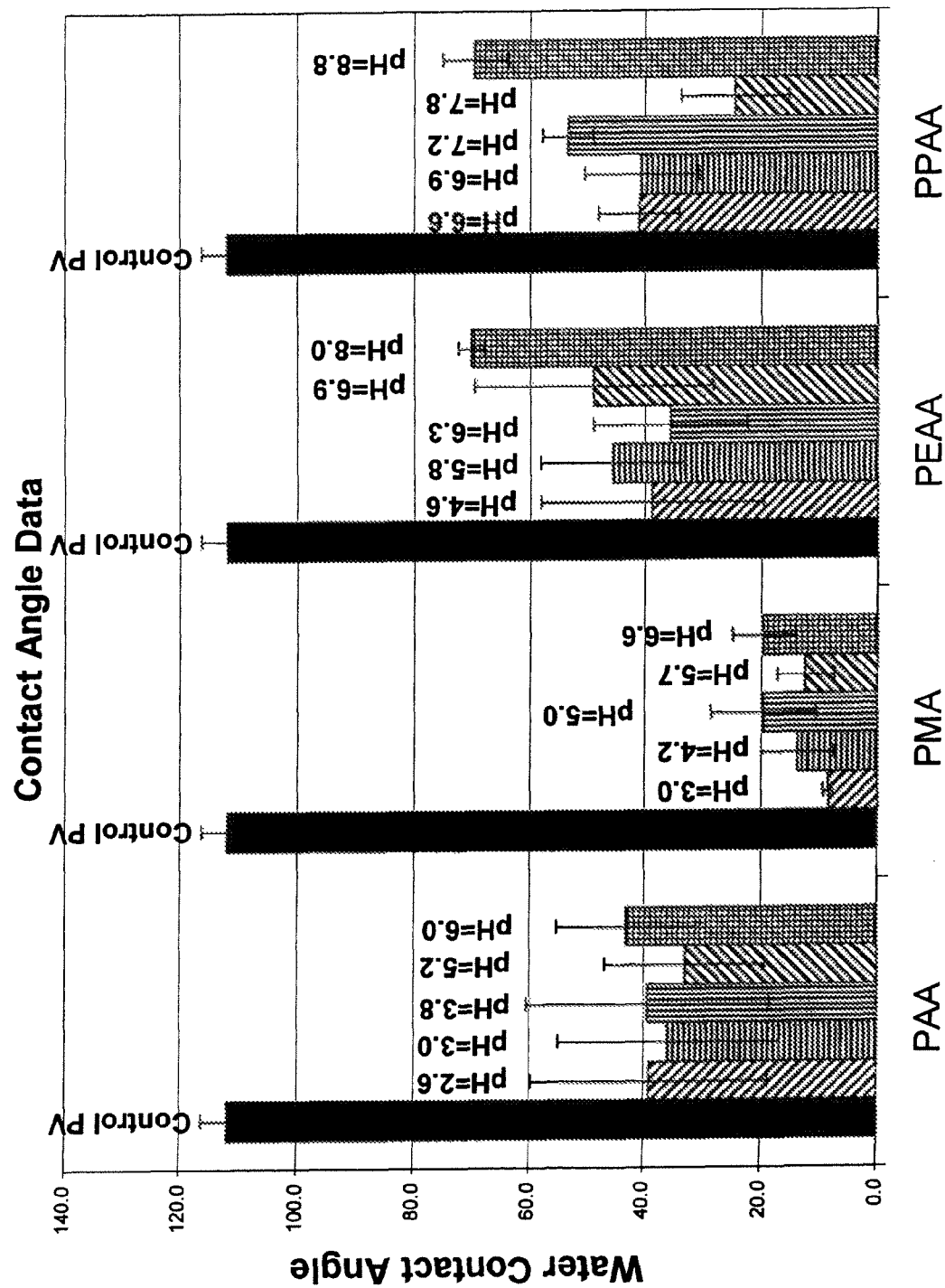
FIG. 5 is a graphical representation showing the contact angle data of a series of poly(carboxylic acid)s.

The results of the contact angle study are shown in FIG. 5. All of the lenses coated with the various poly(carboxylic acid) polymers have a lower water contact angle (i.e., a more wettable lens surface) than the control PureVision® lens. It is also interesting to note that in general, as the hydrophobicity of the substituent in the 2 position was increased, there was an increase in the measured contact angle, possibly due to the hydrophobic nature of the side chain. In addition, the sample that showed silicone levels reapproaching the controls by XPS analysis (PAA at pH of 6.0 and PMAA at pH of 6.6) continue to have low contact angles, possibly due to the fact that little polymer need be present to significantly lower the contact angle when compared to the control.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method comprising:
   (a) immersing an ophthalmic device in a solution comprising a polymer or copolymer having one or more repeating units of the formula:

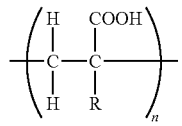

wherein R independently is a $C_2$-$C_{20}$ hydrocarbon radical and n is an integer of 2 to 5000, wherein the solution has an osmolality of at least about 200 mOsm/kg and a pH in the range of about 6 to about 9;
   (b) packaging the solution and the device in a manner preventing contamination of the device by microorganisms; and
   (c) sterilizing the packaged solution and device.

2. The method of claim 1, wherein the biomedical device is a contact lens.

3. The method of claim 1, wherein the biomedical device is a silicone hydrogel contact lens.

4. The method of claim 1, wherein R is a $C_2$-$C_6$ straight chain or branched alkyl group.

5. The method of claim 1, wherein R is an ethyl or propyl group.

6. The method of claim 1, wherein the polymer or copolymer is obtained from the polymerization or copolymerization of a monomeric mixture comprising one or more $C_2$-$C_6$ straight chain, branched, and cyclic 2-alpha-alkyl acrylic acids.

7. The method of claim 6, wherein the monomeric mixture further comprises one or more hydrophilic monomers.

8. The method of claim 1, further comprising hermetically sealing the device and the solution in the package.

9. The method of claim 8, wherein heat sterilization is performed subsequent to sealing of the package.

10. The method of claim 1, wherein the solution does not contain an effective disinfecting amount of a disinfecting agent.

11. The method of claim 1, wherein the solution does not contain a germicide compound.

* * * * *